United States Patent
Rosales et al.

(10) Patent No.: US 8,055,593 B2
(45) Date of Patent: Nov. 8, 2011

(54) LEARNING CLASSIFIERS FOR MULTIPLE-LABEL DATA ANALYSIS

(75) Inventors: Romer E. Rosales, Downingtown, PA (US); Glenn Fung, Madison, WI (US); Mark Schmidt, Athabasca (CA); Sriram Krishnan, Exton, PA (US); R. Bharat Rao, Berwyn, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 709 days.

(21) Appl. No.: 11/877,066

(22) Filed: Oct. 23, 2007

(65) Prior Publication Data

US 2008/0109388 A1    May 8, 2008

Related U.S. Application Data

(60) Provisional application No. 60/856,160, filed on Nov. 2, 2006.

(51) Int. Cl.
*G06F 15/18* (2006.01)
(52) U.S. Cl. ............................................. 706/12
(58) Field of Classification Search .................. None
See application file for complete search history.

(56) References Cited

U.S. PATENT DOCUMENTS

| | | | |
|---|---|---|---|
| 5,768,333 A | 6/1998 | Abdel-Mottaleb | |
| 5,857,030 A | 1/1999 | Gaborski et al. | |
| 6,125,194 A | 9/2000 | Yeh et al. | |
| 7,474,775 B2 | 1/2009 | Abramoff et al. | |
| 7,783,585 B2 * | 8/2010 | Sabe et al. | 706/16 |
| 2005/0187892 A1 * | 8/2005 | Goutte et al. | 707/1 |
| 2008/0301077 A1 * | 12/2008 | Fung et al. | 706/46 |
| 2009/0125461 A1 * | 5/2009 | Qi et al. | 706/12 |

OTHER PUBLICATIONS

Lam, Chuck P. and Stork, David G.; "Toward Optimal Labeling Strategy under Mulitple Unreliable Labelers"; Dec. 1, 2005; American Association for Artificial Intelligence; pp. 1-6.*
Zhu, Shenghou et al.; "Multi-labelled Classification Using Maximum Entropy Method"; 2005; ACM; pp. 1-8.*
Richardson, Matthew and Domingos, Pedro; "Learning with Knowledge from Multiple Experts"; 2003; AAAI Press; pp. 1-8.*
Ghamrawi, Nadia and McCallum, Andrew; "Collective Multi-Label Classification"; 2005; ACM; pp. 195-200.*
Donmez, Pinar et al.; "A Probabilistic Framework to Learn from Multiple Annotators with Time-Varying Accuracy"; pp. 1-12.*
Donmez, Pinar et al.; "Efficiently Learning the Accuracy of Labeling Sources for Selective Sampling"; 2009; ACM; pp. 259-268.*
Taskar, Ben et al.; "Max-Margin Markov Networks"; 2003; MIT Press; pp. 1-8.*
Boutell, et al.; "Learning multi-label scene classification"; 2004; Pattern Recognition 37; pp. 1757-1771.*
Brodley et al.; "Identifying and eliminating mislabeled training instances"; 1996; Thirtheenth National Conference on Artificial Intelligence; Aug. 1996; pp. 799-805 (1-7).*

(Continued)

*Primary Examiner* — David R Vincent
*Assistant Examiner* — Stanley K Hill
(74) *Attorney, Agent, or Firm* — Joshua Ryan (57) ABSTRACT

A method for multiple-label data analysis includes: obtaining labeled data points from more than one labeler; building a classifier that maximizes a measure relating the data points, labels on the data points and a predicted output label; and assigning an output label to an input data point by using the classifier.

15 Claims, 4 Drawing Sheets

OTHER PUBLICATIONS

Friedman et al.; "Additive Logistic Regression: A Statistical View of Boosting"; 2000; The Annals of Statistics 200, vol. 28, No. 2; pp. 337-345.*

Ho et al.; "Decision Combination in Multiple Classifier Systems"; 1994; IEEE Transactions on Pattern Analysis and Machine Intelligence, vol. 16, No. 1; pp. 66-75.*

MacKay, David J. C.; "Information-based objective functions for active data selection"; 1992; MIT Press; Neural Computation, 4; pp. 590-604 (1-14).*

Jin, Rong et al.; "Learning with Multiple Labels"; 2002; MIT Press; Advances in Neural Information Processing Systems 15: Proceedings of the 2002 Conference; 8 pages.*

Belkin, Mikhail et al.; "Regularization and Semi-supervised Learning on Large Graphs"; 2004; Lecture Notes in Computer Science, vol. 3120/2004; pp. 624-638.*

Rifkin, Ryan M. et al.; "Notes on Regularized Least Squares"; 2007; MIT; MIT-CSAIL-TR-2007-025; pp. 1-8.*

Dawid, et al., "Maximum Likelihood Estimation Observer Error-Rates Using EM Algorithm", 2005, American Association for Artificial Intelligence, pp. 1-6.

Jin, et al., "Learning with Multiple Labels", 2002, Advances in Neural Information Processing Systems (NIPS), pp. 1-8.

* cited by examiner

LEARNING CLASSIFIERS FOR MULTIPLE-LABEL DATA ANALYSIS

CROSS-REFERENCE TO RELATED APPLICATION

This application claims the benefit of U.S. Provisional Application No. 60/856,160, filed Nov. 2, 2006, the disclosure of which is incorporated by reference herein in its entirety.

BACKGROUND OF THE INVENTION

1. Technical Field

The present invention relates to multiple-label data analysis.

2. Discussion of the Related Art

In data analysis, it is usually the case that data points are labeled by one labeler (e.g., an expert in the task/data domain), or they are not labeled at all. In general, data points can be any representation of information such as database records, image/text features, documents, biological sequences, etc. A great number of data analysis tasks have been proposed for these situations (e.g., most supervised and unsupervised machine learning algorithms). However, a much less explored area of data analysis involves labels that are provided by multiple labelers, including the case where certain labelers only label some or different data points. Accordingly, there exists a need for providing a data analysis formulation for this situation.

SUMMARY OF THE INVENTION

In an exemplary embodiment of the present invention, a method for multiple-label data analysis comprises: obtaining labeled data points from more than one labeler; building a classifier that maximizes a measure relating the data points, labels on the data points and a predicted output label; and assigning an output label to an input data point by using the classifier.

Building the classifier comprises: defining a functional form of a probability distribution that relates the labels on the data points to the predicted output label; defining a functional form of a probability distribution that relates the predicted output label to the data points; and maximizing a mutual information function by using the defined functional forms to obtain a probability distribution over a plurality of possible predicted output labels given the input data point.

The probability distribution over the plurality of possible predicted output labels defines the classifier. The classifier is deterministic.

Building the classifier comprises: defining a functional form of a probability distribution that relates the labels on the data points to the predicted output label; defining a functional form of a probability distribution that relates the predicted output label to the data points; and optimizing a maximum likelihood based on the data points and the labels on the data points by using the defined functional forms to obtain a probability distribution over a plurality of possible predicted output labels given the input data point.

The probability distribution over the plurality of possible predicted output labels defines the classifier. The classifier is deterministic.

The input data point to which the label is assigned is a newly obtained data point or a previously obtained data point.

The method further comprises: providing, in real-time, a user with the assigned output label; and comparing, at the user-end, the assigned output label to a label input to the data point by the user.

In an exemplary embodiment of the present invention, a computer program product comprises a computer useable medium having computer program logic recorded thereon for multiple-label data analysis, the computer program logic comprising: program code for obtaining labeled data points from more than one labeler; program code for building a classifier that maximizes a measure relating the data points, labels on the data points and a predicted output label; and program code for assigning an output label to an input data point by using the classifier.

The program code for building the classifier comprises: program code for defining a functional form of a probability distribution that relates the labels on the data points to the predicted output label; program code for defining a functional form of a probability distribution that relates the predicted output label to the data points; and program code for maximizing a mutual information function by using the defined functional forms to obtain a probability distribution over a plurality of possible predicted output labels given the input data point.

The probability distribution over the plurality of possible predicted output labels defines the classifier. The classifier is deterministic.

The program code for building the classifier comprises: program code for defining a functional form of a probability distribution that relates the labels on the data points to the predicted output label; program code for defining a functional form of a probability distribution that relates the predicted output label to the data points; and program code for optimizing a maximum likelihood based on the data points and the labels on the data points by using the defined functional forms to obtain a probability distribution over a plurality of possible predicted output labels given the input data point.

The probability distribution over the plurality of possible predicted output labels defines the classifier. The classifier is deterministic.

The input data point to which the label is assigned is a newly obtained data point or a previously obtained data point.

The computer program product further comprises: program code for providing, in real-time, a user with the assigned output label; and program code for enabling comparison, by the user, of the assigned output label to a label input to the data point by the user.

In an exemplary embodiment of the present invention, a method for analyzing data labeled by multiple-experts comprises: receiving a training dataset, wherein the training dataset includes labeled data points that are labeled by more than one expert-labeler; training a classifier that maximizes a measure relating a predicted label, the labels on the data points and the data points, wherein the classifier assigns a different weight to each expert based on expert-specific parameters; and assigning an output label to an input data point by inputting the input data point to the classifier.

The method further comprises: grouping the experts based on the expert-specific parameters; and assigning a different weight to a group of experts based on their grouping. The method further comprises retraining the classifier using newly provided labels or newly provided labeled data points.

The foregoing features are of representative embodiments and are presented to assist in understanding the invention. It should be understood that they are not intended to be considered limitations on the invention as defined by the claims, or limitations on equivalents to the claims. Therefore, this summary of features should not be considered dispositive in determining equivalents. Additional features of the invention will become apparent in the following description, from the drawings and from the claims.

DETAILED DESCRIPTION OF EXEMPLARY EMBODIMENTS

Presented herein are two formulations for learning classifiers to be employed when performing multiple-label data analysis. The description of these formulations will begin with a description of the multi-label problem, followed by a description of two separate methods for building the classifiers, a summary of the invention including a description of building and using the classifiers for multiple-label data analysis, a description of some specific scenarios in which the invention may be implemented and a discussion of several extensions of the invention.

Proposed Multi-Label Problem and Approaches

We are given N data points $\{x_1, \ldots, x_N\}$, where $x_k$ is in some domain $\mathcal{X}$, labeled by T (or less) labelers (e.g., doctors). The label for the i-th data point given by doctor t is denoted by $y_i^{(t)} \in \mathcal{Y}$. The labels to be found/proposed by our algorithm or classifier are denoted by $z_i \in \mathcal{Z}$ (normally $\mathcal{Y} = \mathcal{Z}$). Given some training dataset, our goal is to find a classifier (or a probability distribution over random variables X and Z) that maximizes some measure relating the predicted label and the labels given by the different labelers. In the following sections, we describe various criteria for obtaining these classifiers (and for using the obtained classifiers).

Maximizing Mutual Information Between Classifier and Expert Labels

In the first formulation, let us define the random variables $Y^{(t)}$ over the space of labels $\mathcal{Y}$, provided by the labeler t, for $t=\{1, \ldots, T\}$. Similarly, let us define the random variables $X \in \mathcal{X}$ and $Z \in \mathcal{Z}$ to represent input data points (observed) and unknown output respectively. Note that for a given data point some of these variables may be unobserved. Some labels may not be observed or provided for some labeler t.

In the approach in this section we use the concept of mutual information (as described, for example, in T. M. Cover and J. A. Thomas, Elements of information theory, Wiley-InterScience, 1991). We are interested in maximizing the information provided by the label z output by our algorithm about the labels provided by the labelers y. Specifically:

$$\underset{p(z|x)}{\operatorname{argmax}} I(Y; Z | X), \quad (1)$$

where we use Y to represent $Y^{(1)}, \ldots, Y^{(T)}$.

We first concentrate on one specific instance of the general criteria. By using a probabilistic graphical model (as described, for example, in J. Pearl, Probabilistic reasoning in intelligent systems, Morgan-Kaufman, 1988) of the form $X \rightarrow Z \rightarrow Y^{(T)}$, thus for one (any) labeler t the criterion can be simplified to:

$$\underset{p(z|x)}{\operatorname{argmax}} I(Y; Z | X) \quad (2)$$

$$\operatorname{argmax} H(Y | X) - H(Y | Z, X) \quad (3)$$

$$= \operatorname{argmax} \sum_{x,y,z} p(y|z) p(z|x) p(x) \log p(y|z) \quad (4)$$

$$= \operatorname{argmax} \sum_i \sum_{z_i} p(y_i|z_i) p(z_i|x_i) \log p(y_i|z_i) \quad (5)$$

$$= \operatorname{argmax} \sum_{t,i} \sum_{z_i} p(y_i^{(t)}|z_i) p(z_i|x_i) \log p(y_i^{(t)}|z_i) \quad (6)$$

where the last equation arises by assuming the labeler responses are independent given the observed input data.

The above is a general approach. We can further specify this model by defining the conditional probability: $y^{(t)}|z \sim N(y^{(t)}:z, \sigma^2$ and a deterministic classifier (i.e., $p(z_i|x_i)$ takes the values of zero or one) denoted by $f: \mathcal{X} \rightarrow \mathcal{Z}$, with parameters $\theta$. This generates the following problem:

$$\operatorname{argmax} \sum_{t,i} p(y_i^{(t)} | z_i \equiv f(x_i; \theta)) \log p(y_i^{(t)} | z_i) \quad (7)$$

$$\underset{\theta}{\operatorname{argmax}} \sum_t \sum_i \log p(y_i^{(t)} | f(x_i; \theta)) \quad (8)$$

$$\underset{\theta,\sigma}{\operatorname{argmin}} \frac{1}{\sigma^2} \sum_t \sum_i (y_i^{(t)} - f(x_i; \theta))^2 + \log|\sigma| \quad (9)$$

Now if you assume a Gaussian distribution, but different for each labeler, we obtain:

$$\underset{\theta,\{\sigma_t\}}{\operatorname{argmin}} \sum_t \frac{1}{\sigma_t^2} \sum_i (y_i^{(t)} - f(x_i; \theta))^2 + \log|\sigma_t| \quad (10)$$

A mean parameter can be added per labeler also. The above is a way to automatically put different effort into classifying each doctor's cases correctly. Since each doctor is considered different, and has their own biases and preferences, an automatic classifier must take into account these biases. However, note that these biases are not stated explicitly (given beforehand), but could be automatically calculated by the algorithm that solves Equation 10.

Note that the expression in Equation 10 can be optimized iteratively by finding $\theta$ first. Given $\theta$, $\sigma$ can be found easily, since each problem is convex when the appropriate variable is fixed.

Once the parameters $\theta$ have been found (learning stage), a new data point x can be classified simply using $z=f(x; \theta)$, where z is the proposed class label or score (if a score, this needs to be further discretized to obtain a class label).

Maximizing Likelihood of the Observed Data

The second formulation involves solving a maximum likelihood problem. The goal is to maximize the probability of the observed data. For now, let us assume that all labelers label all points (this restriction can be eliminated later at the expense of computation time). We propose to solve the following problem:

$$\underset{\theta}{\operatorname{argmax}} \prod_t \prod_i p(x_i, y_i^{(t)}; \theta), \quad (11)$$

where $\theta$ represents all the parameters of the distribution.

If we use a probability model of the form $X \rightarrow Z - Y^{(t)}$ (and maximize the logarithm of the previous equation), we have the following equivalent problem:

$$\underset{\theta}{\operatorname{argmax}} \sum_t \sum_i \log \sum_{z_i} p(x_i, y_i^{(t)}, z_i; \theta) \quad (12)$$

This can be solved by defining the following Expectation Maximization (EM) Algorithm.

E-step: Compute $\tilde{p}(z_i) \equiv p(z_i | x_i, y_i)$ $$\tilde{p}(z_i) \propto \prod_t p(y_i^{(t)} | z_i) p(z_i | x_i), \quad (13)$$

note here that if $y_i^{(u)}$ is missing, we simply do not consider that observation.

M-step: maximize $\Sigma_t \Sigma_i E_{\tilde{p}(z_i)}[\log p(x_i, y_i^{(t)}, z_i)]$. The difficulty of this optimization depends on the specific form of the probabilities $p(y_i^{(t)}|z_i)$ and $p(z_i|x_i)$.

We can define an instance of the problem by specifying:

$$p(y_i^{(t)}|z_i) = N(y_i^{(t)}; z_i, \sigma_t) \quad (14)$$

$$p(z_i = 1|x_i) = 1/1 + e^{-(\alpha x_i + \beta)}, \quad (15)$$

which correspond to a Gaussian conditional distribution for the labeler-provided label given the classifier output, and a logistic registration model for the classifier (class label conditioned on input features). In the above case, the classification problem is assumed binary, but logistic regression extensions for multiple classes are known in the literature and could also be used.

The learning-stage algorithm consists of iterating E and M steps. In the above case, the M-step can be implemented by maximizing over the parameters of $p(y_i^{(t)}|z_i)$ and $p(z_i|x_i)$ in a sequential form by fixing the parameters of one distribution at a time.

For the case of logistic registration, once the parameters $\alpha$, $\beta$ have been found (learning stage), a new data point x can be classified simply by letting $p(z=1|x) = 1/1 + e^{-(\alpha x + \beta)}$, where $z=1$ is the class label of interest.

Summary, Specific Scenarios, and Extensions

In this section we will summarize the ideas presented in this invention disclosure, include a description of building and using the classifiers for multiple-label data analysis, describe some specific scenarios in which the invention may be implemented and discuss several extensions of the invention.

In sum, we have proposed to build a classifier, consisting of the steps of:
1. Obtaining labels from more than one labeler, where each labeler labels at least one data point (e.g., case, image, record, etc.) and a label may be, for example, a mark on an image indicating a medical condition, or a mark in a patient's record indicating the patient's name, prior medical history, current diagnosis, etc.
2. Building a classifier that maximizes some measure relating the predicted label and the labels given by each of the different labelers.

The classifier can be built using the methods and measures described in the above sections entitled "Maximizing mutual information between classifier and expert labels" and "Maximizing likelihood of the observed data".

A description of a method for building and using the classifiers for multiple-label data analysis will now be provided.

Figure 1:
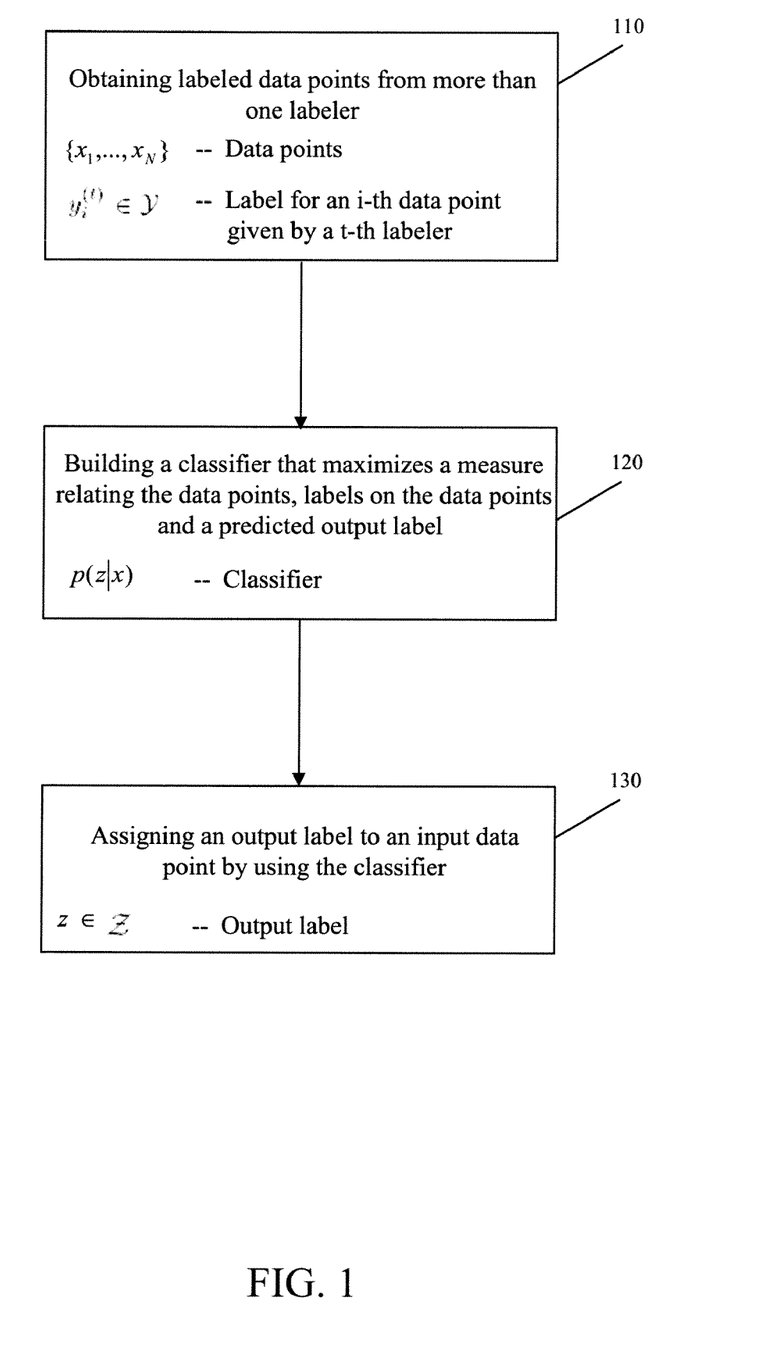
FIG. 1 is a flowchart of a method for multiple-label data analysis according to an exemplary embodiment of the present invention.

As shown in FIG. 1, labeled data points are obtained from more than one labeler, wherein $\{x_1, \ldots, x_n\}$ represent the data points and $y_i^{(t)} \in Y$ represents a label for an i-th label given by a t-th labeler (110). A classifier $p(z|x)$ that maximizes a measure relating the data points, labels on the data points and a predicted output label is built (120). An output label $z \in \mathcal{Z}$ is then assigned to an input data point by using the classifier (130).

Figure 2A:
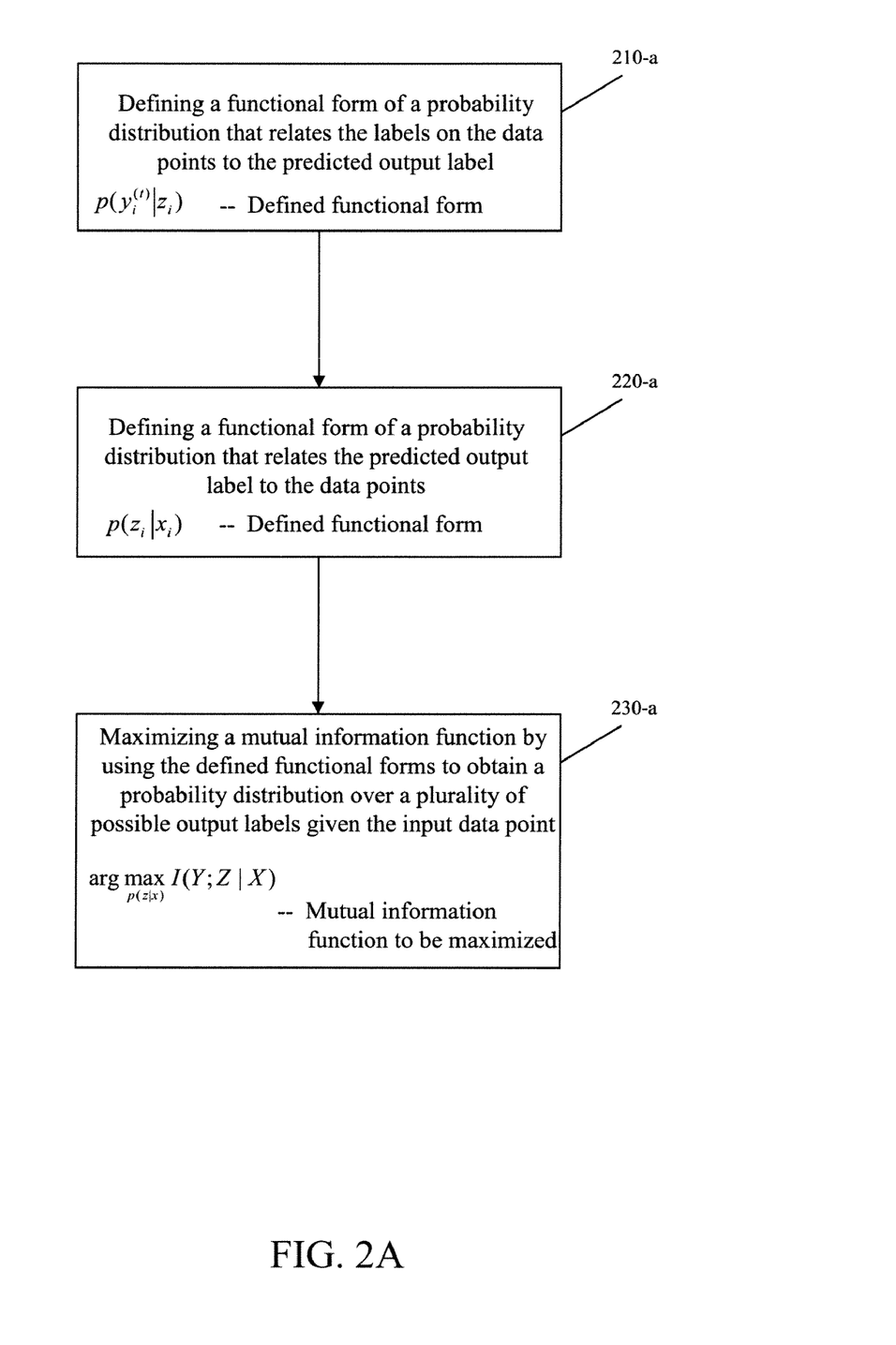
FIG. 2A is a flowchart of a method for building a learning classifier according to an exemplary embodiment of the present invention.

FIG. 2A illustrates the steps of building a classifier in step 120. These steps refer to building the classifier described in the above section entitled "Maximizing mutual information between classifier and expert labels".

As shown in FIG. 2A, a functional form of a probability distribution that relates the labels on the data points to the predicted output label is defined, wherein $p(y_i^{(t)}|z_i)$ represents the defined functional form (210-a). A functional form of a probability distribution that relates the predicted output label to the data points is defined, wherein $p(z_i|x_i)$ represents the defined functional form (220-a). A mutual information function is maximized by using the defined functional forms to obtain a probability distribution over a plurality of possible output labels given the input data point, wherein $$\underset{p(z|x)}{\operatorname{argmax}} I(Y; Z | X)$$

represents the mutual information function to be maximized (230-a).

Figure 2B:
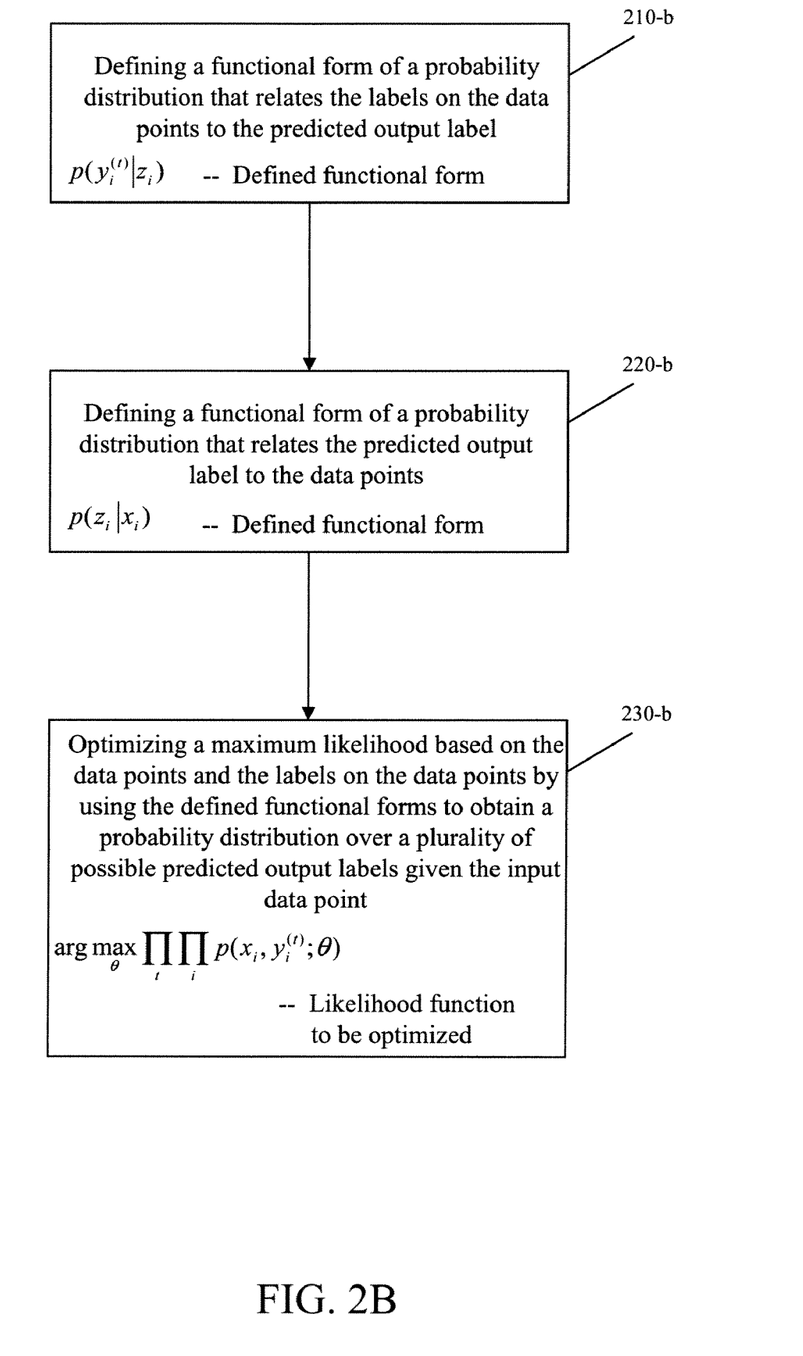
FIG. 2B is a flowchart of a method for building a learning classifier according to an exemplary embodiment of the present invention.

FIG. 2B illustrates the steps of building another classifier in step 120. These steps refer to building the classifier described in the above section entitled "Maximizing likelihood of the observed data".

As shown in FIG. 2B, a functional form of a probability distribution that relates the labels on the data points to the predicted output label is defined, wherein $p(y_i^{(t)}|z_i)$ represents the defined functional form (210-b). A functional form of a probability distribution that relates the predicted output label to the data points is defined, wherein $p(z_i|x_i)$ represents the defined functional form (220-b). A maximum likelihood is optimized based on the data points and the labels on the data points by using the defined functional forms to obtain a probability distribution over a plurality of possible predicted output labels given the input data point, wherein $$\underset{\theta}{\operatorname{argmax}} \prod_t \prod_i p(x_i, y_i^{(t)}; \theta)$$

represents the likelihood function to be optimized (230-b). The likelihood function may be computed by repeating these steps: 1) compute $\tilde{p}(z_i) \equiv p(z_i|x_i, y_i)$; and 2) maximize $$\sum_t \sum_i E_{\tilde{p}(z_i)}[\log p(x_i, y_i^{(t)}, z_i)]$$

to obtain distribution $p(z_i|x_i)$.

We now describe some specific scenarios in which the invention may be implemented and as well as several extensions of the invention.

In an on-line scenario, information from additional labelers can be incorporated to an already built classifier. For example, the labeler provides his input and this is taken into consideration as one of many labels already provided to the classifier. In some instances, it is also possible to retrain the classifier without having to reuse all of the old labels, but only the newly provided labels.

One of the general ideas in this invention disclosure is that of treating the different labelers differently based on the information provided (at least) by their labels, but other (e.g., labeler known background information) can be used. In particular, this is done for addressing multi-label problems and profiting from datasets with multiple labels in general. This can be accomplished in various ways. One approach is to automatically calculate labeler specific parameters such as biases and particular tendencies, so that they are accounted for in an appropriate manner (e.g., using a probabilistic model) by the learning algorithm and later the classifier. These parameters can be estimated automatically (numerically), as formulated above, but they can also be set according to a predetermined level of expertise assigned to the labeler (e.g., the credentials of a doctor). This can result in a classifier that assigns a different level of contribution to each labeler. One instance of this is when each labeler gets an assigned a weight (or strength) for contributing to classifier training and/or for the final classification result.

In general, we expect to obtain better classification performance by incorporating/estimating this type of information as compared to ignoring labeler parameters or variables (independently of whether these are determined automatically).

One proposed application setting of interest is medical diagnosis, where usually different medical experts provide their opinion regarding a given patient or case (e.g., by looking at an ultrasound image, or by looking at doctor notes, lab reports, etc.). While the source data can be different (e.g., images or documents/text), the approaches discussed in this paper are appropriate for any of these settings.

At the application level, we can further consider a method for, on-line or off-line, collaborative labeling, where the output of the above classifier analysis is used. For example, we can compare a label provided by a labeler with the label predicted by the classifier and inform the labeler of this prediction. Further, the labeler can be informed of the label given by some (or all) of the labelers, for which this information has been collected.

In the medical domain, this classification method can also be incorporated into the physician workflow. It can be used to compare the physician assessment with that given by the classifier or other doctors. It can further be used for medical training, since the automatic classifier can be seen as a way to summarize the knowledge given by the different experts (involved in the classifier construction).

Note that the problem above does not need to limit the type of information each labeler uses to identify labels for the data points. If different labelers observe different features (or information in general) for each data point, this information can be provided to the classifier as well during the learning stage. The classifier need not have all of the features at classification time, since these can be treated as hidden variables (in both formulations above).

In addition to treating each labeler differently, we can extend this idea to treating labelers by group, where the grouping corresponds to any attribute of interest.

A system in which exemplary embodiments of the present invention may be implemented will now be described.

Figure 3:
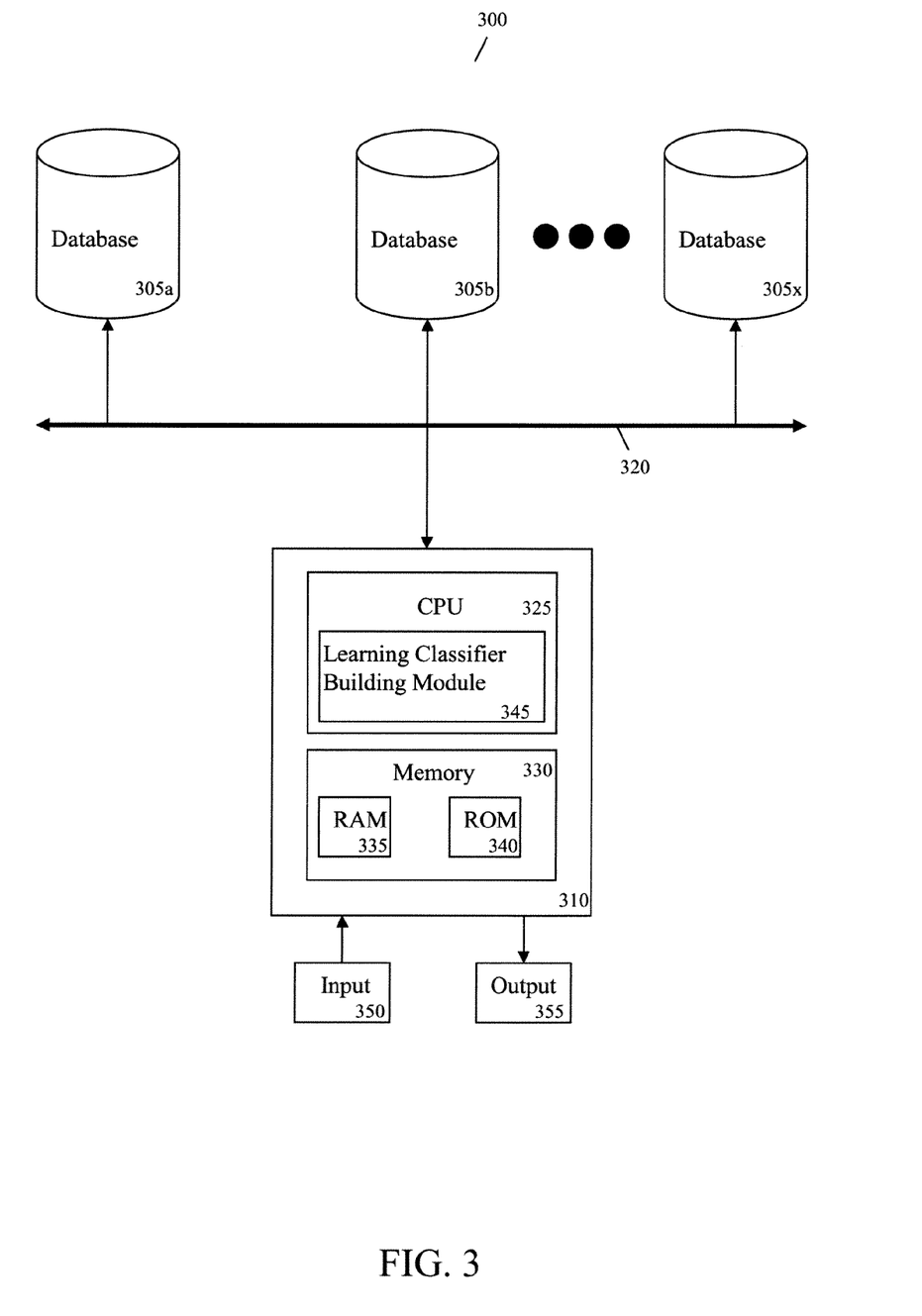
FIG. 3 is a block diagram of a system in which exemplary embodiments of the present invention may be implemented.

As shown in FIG. 3, the system 300 includes a plurality of databases 305a, b, ..., x and a personal computer (PC) 310 connected over, for example, a wired or wireless network 320.

The databases 305a, b, ..., x are used to store information associated with data points such as what labels are provided for the data points and who labeled the data points. These databases 305a, b, ..., x may be local or remotely accessible by the PC 310.

The PC 310, which may be a portable or laptop computer, a medical diagnostic imaging system or a picture archiving communications system (PACS) data management station, includes a central processing unit (CPU) 325 and a memory 330 which are connected to an input device 350 and an output device 355. The CPU 325 includes a learning classifier building module 345 that includes software for executing methods in accordance with exemplary embodiments of the present invention.

The memory 330 includes a random access memory (RAM) 335 and a read-only memory (ROM) 340. The memory 330 can also include a database, disk drive, tape drive, etc., or a combination thereof. The RAM 335 functions as a data memory that stores data used during execution of a program in the CPU 325 and is used as a work area. The ROM 340 functions as a program memory for storing a program executed in the CPU 325. The input 350 is constituted by a keyboard, mouse, etc., and the output 355 is constituted by a liquid crystal display (LCD), cathode ray tube (CRT) display, printer, etc.

It should be understood that the present invention may be implemented in various forms of hardware, software, firmware, special purpose processors, or a combination thereof. In one embodiment, the present invention may be implemented in software as an application program tangibly embodied on a program storage device (e.g., magnetic floppy disk, RAM, CD ROM, DVD, ROM, and flash memory). The application program may be uploaded to, and executed by, a machine comprising any suitable architecture.

It is to be further understood that because some of the constituent system components and method steps depicted in the accompanying figures may be implemented in software, the actual connections between the system components (or the process steps) may differ depending on the manner in which the present invention is programmed. Given the teachings of the present invention provided herein, one of ordinary skill in the art will be able to contemplate these and similar implementations or configurations of the present invention.

In addition, the above description is only representative of illustrative embodiments. For the convenience of the reader, the above description has focused on a representative sample of possible embodiments, a sample that is illustrative of the principles of the invention. The description has not attempted to exhaustively enumerate all possible variations. That alternative embodiments may not have been presented for a specific portion of the invention, or that further undescribed alternatives may be available for a portion, is not to be considered a disclaimer of those alternate embodiments. Other applications and embodiments can be implemented without departing from the spirit and scope of the present invention.

It is therefore intended, that the invention not be limited to the specifically described embodiments, because numerous permutations and combinations of the above and implementations involving non-inventive substitutions for the above can be created, but the invention is to be defined in accordance with the claims that follow. It can be appreciated that many of those undescribed embodiments are within the literal scope of the following claims, and that others are equivalent.

What is claimed is:

1. A method for multiple-label data analysis, comprising:
    obtaining labeled data points from more than one labeler, wherein at least one data point is labeled by more than one labeler;
    building a classifier that maximizes a measure relating the data points and labels on the data points to a predicted output label; and
    assigning an output label to an input data point by using the classifier,
    wherein the method is performed using a processor;

wherein building the classifier comprises solving the following equation $$\underset{\theta,\{\sigma_t\}}{\operatorname{argmin}} \sum_t \frac{1}{\sigma_t^2} \sum_i (y_i^{(t)} - f(X_i;\theta))^2 + \log|\sigma_t|$$

where $y_i^{(t)}$ is a label for an i-th data point given by a t-th labeler and $x_i$ is the i-th data point and $\theta$ and $\sigma$ are parameters of the classifier that are determined by solving the equation.

2. The method of claim 1, wherein building the classifier comprises:
defining a functional form of a probability distribution that relates the labels on the data points to the predicted output label;
defining a functional form of a probability distribution that relates the predicted output label to the data points; and
maximizing a mutual information function by using the defined functional forms and the solution to the optimization problem to obtain a probability distribution over a plurality of possible predicted output labels given the input data point.

3. The method of claim 2, wherein the probability distribution over the plurality of possible predicted output labels defines the classifier.

4. The method of claim 3, wherein the classifier is deterministic.

5. The method of claim 1, wherein the input data point to which the label is assigned is a newly obtained data point or a previously obtained data point.

6. The method of claim 1, further comprising:
providing, in real-time, a user with the assigned output label; and
comparing the assigned output label to a label input to the data point by the user.

7. A computer program product comprising a non-transitory computer useable medium having computer program logic recorded thereon for multiple-label data analysis, the computer program logic comprising:
program code for obtaining labeled data points from more than one labeler, wherein at least one data point is labeled by more than one labeler;
program code for building a classifier that maximizes a measure relating the data points and labels on the data points to a predicted output label; and
program code for assigning an output label to an input data point by using the classifier,
wherein building the classifier comprises solving the following equation $$\underset{\theta,\{\sigma_t\}}{\operatorname{argmin}} \sum_t \frac{1}{\sigma_t^2} \sum_i (y_i^{(t)} - f(x_i;\theta))^2 + \log|\sigma_t|$$

where $y_i^{(t)}$ is a label for an i-th data point given by a t-th labeler and $x_i$ is the i-th data point, and $\theta$ and $\sigma$ are parameters of the classifier that are determined by solving the equation.

8. The computer program product of claim 7, wherein the program code for building the classifier comprises:

program code for defining a functional form of a probability distribution that relates the labels on the data points to the predicted output label;
program code for defining a functional form of a probability distribution that relates the predicted output label to the data points; and
program code for maximizing a mutual information function by using the defined functional forms and the solution of the equation to obtain a probability distribution over a plurality of possible predicted output labels given the input data point.

9. The computer program product of claim 8, wherein the probability distribution over the plurality of possible predicted output labels defines the classifier.

10. The computer program product of claim 9, wherein the classifier is deterministic.

11. The computer program product of clam 7, wherein the input data point to which the label is assigned is a newly obtained data point or a previously obtained data point.

12. The computer program product of claim 7, further comprising:
program code for providing, in real-time, a user with the assigned output label; and
program code for enabling comparison, by the user, of the assigned output label to a label input to the data point by the user.

13. A method for analyzing data labeled by multiple-experts, comprising:
receiving a training dataset, wherein the training dataset includes labeled data points from expert-labelers, wherein at least one data point is labeled by more than one expert-labeler;
training a classifier that maximizes a measure relating a predicted label to the labels on the data points and the data points, wherein the classifier assigns a different weight to each expert based on expert-specific parameters; and
assigning an output label to an input data point by inputting the input data point to the classifier,
wherein the method is performed using a processor,
wherein building the classifier comprises solving by the following equation $$\underset{\theta,\{\sigma_t\}}{\operatorname{argmin}} \sum_t \frac{1}{\sigma_t^2} \sum_i (y_i^{(t)} - f(x_i;\theta))^2 + \log|\sigma_t|$$

where $y_i^{(t)}$ is a label for an i-th data point given by a t-th labeler and $x_i$ is the i-th data point, and $\theta$ and $\sigma$ are parameters of the classifier that are determined by solving the equation.

14. The method of claim 13, further comprising:
grouping the experts based on the expert-specific parameters; and
assigning a different weight to a group of experts based on their grouping.

15. The method of claim 13, further comprising:
retraining the classifier using newly provided labels or newly provided labeled data points.

* * * * *